US005658730A

United States Patent [19]
McGill et al.

[11] Patent Number: 5,658,730
[45] Date of Patent: Aug. 19, 1997

[54] METHODS OF HUMAN PROSTATE CANCER DIAGNOSIS

[75] Inventors: John McGill, Boerne; Carla Van Den Berg, San Antonio, both of Tex.; Jeffrey Trent, Rockville, Md.; Daniel Von Hoff, San Antonio, Tex.; Paul Meltzer, Potomac, Md.

[73] Assignee: CTRC Research Foundation, San Antonio, Tex.

[21] Appl. No.: 376,364

[22] Filed: Dec. 23, 1994

[51] Int. Cl.$^6$ .............................. C12Q 1/68; C07H 21/04
[52] U.S. Cl. .............................. 435/6; 536/24.31; 436/64; 436/813; 935/78
[58] Field of Search .............................. 435/6; 536/24.31, 536/24.33; 436/64, 813; 935/77, 78

[56] References Cited

PUBLICATIONS

Denis, European Urology (1993) 24: 13–18.
Takahashi et al Cancer Research (1994) 54: 3574–3579.
Alcaraz et al., "Aneuploidy and Aneusomy of Chromosome 7 Detected by Fluorescence in Situ Hybridization Are Markers of Poor Prognosis in Prostate Cancer," *Cancer Research*, 54:3998–402, 1994.
Bova et al., "Homozygous Deletion and Frequent Allelic Loss of Chromosome 8p22 Loci in Human Prostate Cancer," *Cancer Research*, 53:3869–3873, 1993.
Brothman et al., "Frequency and Pattern of Karyotypic Abnormalities in Human Prostate Cancer," *Cancer Research*, 50:3795–3803, 1990.
Fukumoto et al., "Analysis of Gene Amplification in Human Tumor Cell Lines," *Genetics*, 85:6846–6850, 1988.
Guan et al., "Generation of Bank–Specific Painting Probes from a Single Microdissected Chromosome," *Human Molecular Genetics*, 2(8):1117–1121, 1993.
Guan et al., "Identification of Cryptic Sites of DNA Sequence Amplification in Human Breast Cancer by Chromosome Microdissection," *Nature Genetics*, 8:155–161, 1994.
Kallioniemi et al., "Comparative Genomic Hybridization for Molecular Cytogenetic Analysis of Solid Tumors," *Science*, 258:818–821, 1992.
Kallioniemi et al., "Optimizing Comparative Genomic Hybridization for Analysis of DNA Sequence Copy Number Changes in Solid Tumors," *Genes, Chromosomes and Cancer*, 10:231–24, 1994.
Lüdecke et al., "Cloning Defined Regions of the Human Genome by Microdissection of Banded Chromosomes and Enzymatic Amplification," *Nature*, 338:348–350, 1989.
Macoska et al., "Fluorescence in Situ Hybridization Analysis of 8p Allelic Loss and Chromosome 8 Instability in Human Prostate Cancer," *Cancer Research*, 54:3824–3830, 1994.
Meltzer et al., "Rapid generation of region specific probes by chromosome microdissection and their application," *Nature Genetics*, 1:24–28, 1992.
Milašin and Mićić, "Double Minute Chromosomes in an Invasive Adenocarcinoma of the Prostate," *Cancer Genet Cytogenet*, 72:157–159, 1994.
Pelicci et al., "Amplification of N–myc in Untreated Human neuroblastomas Correlates with Advanced Disease Stage," *Science*, 224:1121–1124, 1984.
Persons et al., "Use of Fluorescent in Situ Hybridization for Deoxyribonucleic Acid Ploidy Analysis of Prostatic Adenocarcinoma," *Journal of Urology*, 150:120–125, 1993.
Pinkel et al., "Cytogenetic Analysis Using Quantitative, High–Sensitivity, Fluorescence Hybridization," *Proc. Natl. Acad. Sci. USA*, 83:2934–2938, 1986.

(List continued on next page.)

*Primary Examiner*—W. Gary Jones
*Assistant Examiner*—Carla Myers
*Attorney, Agent, or Firm*—Arnold, White & Durkee

[57] ABSTRACT

Disclosed are diagnostic techniques for the detection of human prostate cancer. Genetic probes and methods useful in monitoring the progression and diagnosis of prostate cancer are described. The invention relates particularly to hybridization methods for evaluating the prevalence of gene amplification in a limited regions of human chromosome 8q24.

24 Claims, 4 Drawing Sheets

OTHER PUBLICATIONS

Visakorpi et al., "Sensitive Detection of Chromosome Copy Number Aberrations in Prostate Cancer by Fluorescence in Situ Hybridization," *American Journal of Pathology*, 145(3):624–630, 1994.

Zhang et al., "Rapid Isolation and Characterization of Amplified DNA by Chromosome Microdissection: Identification of IGF1R Amplification in Malignant Melanoma," *Oncogene*, 8:2827–2831, 1993.

Zhang et al., "Whole Genome Amplification from a Single Cell: Implications for Genetic Analysis," *Proc. Natl. Acad. Sci. USA*, 89:5847–5851, 1992.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: modified_base ( B ) LOCATION: 10..15
( D ) OTHER INFORMATION: /mod_base=OTHER
/ note= "N = A, G, C, or T"

( x i ) SEQUENCE DESCRIPTION: SEQ ID NO:1:

CCGACTCGAG NNNNNNATGT GG                                                                              2 2

METHODS OF HUMAN PROSTATE CANCER DIAGNOSIS

The United States government has certain rights in the present invention pursuant to Grant P20CA58225 from the National Cancer Institute.

BACKGROUND OF THE INVENTION

A. Field of the Invention

The present invention relates generally to methods and nucleic acid sequences useful as probes for the identification of a region within human chromosome 8q24. The invention also relates to diagnostic techniques for the detection of particular forms of human cancer. More particularly, it concerns probes and methods useful in monitoring the progression of prostate cancer through the use of fluorescence in situ hybridization techniques.

B. Description of the Related Art

Carcinoma of the prostate (PCA) is the second-most frequent cause of death in men in the United States (Boring, 1994). The increased incidence of prostate cancer during the last decade has established prostate cancer as the most prevalent of all cancers (Carter and Coffey, 1990). Although prostate cancer is the most common cancer found in United States men, (approximately 200,000 newly diagnosed cases/year), the molecular changes underlying its genesis and progression remain poorly understood (Boring et al., 1993). According to American Cancer Society estimates, the number of deaths from PCA is increasing in excess of 8% annually.

Unfortunately, due to the extreme variability in the natural history of this disease, coupled to frequent incidental diagnosis of subclinical disease (following prostate-specific antigen [PSA] testing or transurethral resection for urinary obstruction) no genetic markers have been identified which could discriminate prostate cancers likely to progress to lethal metastatic disease (Ruckle et al., 1993).

Furthermore, the ability to accurately assay the metastatic spread of an individual tumor of the prostate is also not available. Genetic alterations have not been identified that could serve as prognostic markers relevant to clinical decision-making. Although clinical and pathologic stage and histological grading systems (e.g., Gleason's) have been used to indicate prognosis for groups of patients based on the degree of tumor differentiation or the type of glandular pattern (Carter and Coffey, 1989; Diamond et al., 1982), these systems do not predict the progression rate of the cancer. While the use of computer-system image analysis of histologic sections of primary lesions for "nuclear roundness" has been suggested as an aide in the management of individual patients (Diamond et al., 1982), this method is of limited use in studying the progression of the disease.

The analysis of DNA content/ploidy using flow cytometry, and fluorescence in situ hybridization (FISH) have recently been demonstrated to have utility as a marker of prostate cancer aggressiveness (Pearsons et al., 1993; Macoska et al., 1994; Visakorpi et al., 1994; Takahashi et al., 1994; Alcaraz et al., 1994; Pearsons et al., 1993), but these methods are expensive, time-consuming, and the latter methodology requires the construction of centromere-specific probes for analysis. Finally, despite the use of comparative genomic hybridization (CGH) in prostate cancer specimens, characteristics that distinguish aggressive versus indolent PCA remain unclear.

The inability to identify patients who are more likely to progress or do poorly despite therapy causes both uncertainty and disappointment in clinical management of patients with such cancer.

In human breast cancer, the presence of particular gene(s) has been linked to indication of disease progression. One such example is the detection of a human breast cancer gene on chromosome 17 (17q21) (Miki, et al. 1994; Futreal et al. (1994). Unfortunately, no study has identified similar important genes in prostate cancer. Although extrachromosomal dmins have been reported in some prostate tumor specimens (Brothman et al., 1990; Lundgren et al., 1992; Milasin et al., 1994), no evidence of chromosomal gene amplification of known oncogenes has yet been reported.

Recent studies have identified several recurring genetic changes in prostate cancer including: 1) allelic loss (particularly loss of chromosome 8p and 16q) (Bova, et al., 1993; Macoska et al., 1994; Carter et al., 1990); 2) generalized DNA hypermethylation (Isaacs et al., 1994); 3) point mutations or deletions of the retinoblastoma (Rb) and p53 genes (Bookstein et al., 1990a; Bookstein et al., 1990b; Isaacs et al., 1991); 4) alterations in the level of certain cell-cell adhesion molecules (i.e., E-cadherin/alpha-catenin) (Carter et al., 1990; Morton et al., 1993; Umbas et al., 1992) and aneuploidy and aneusomy of chromosomes detected by FISH, particularly chromosomes 7 and 8(Macoska et al., 1994; Visakorpi et al., 1994; Takahashi et al., 1994; Alcaraz et al., 1994). It seems certain, that a combination of these changes is critical to the acquisition of metastatic potential, and Isaacs and colleagues (Isaacs et al., 1994) have recently proposed a model placing these genetic changes in the context of prostate cancer disease progression.

One approach to the analysis of amplified DNA sequences has relied on DNA electrophoresis (e.g., in gel renaturation or restriction landmark genomic scanning). While these techniques successfully identify amplified sequences, they are extremely laborious and can be confounded by amplified sequences unrelated to the phenotype of interest.

These and other inherent deficiencies in the prior art evidences the tremendous need in the medical arts not only for the identification of the gene linked with the progression of prostate cancer, but also the need for a diagnostic method to monitor this progression. Likewise, the identification of a commonly amplified chromosome region in prostate cancer would be of considerable importance, and the development of a rapid, inexpensive method to detect such amplification would provide a significant contribution to the area of cancer diagnosis, monitoring, and treatment.

SUMMARY OF THE INVENTION

The present invention addresses these and certain other deficiencies in the prior art in having identified and characterized a common region of gene amplification in human prostate cancer cells. In particular, a method is provided that utilizes nucleic acid probes for the detection of genetic amplification in prostate cancer cells at regions of chromosome 8q24. Gene amplification in this region has been linked to prostate cancer progression, and thus characterization of this amplification represents an important molecular genetic tool in monitoring the progress of prostate cancer.

The present invention identifies for the first time, DNA sequence copy number changes of chromosome 8q as a marker of likely significance for the development of aggressive prostate cancers. Using chromosome microdissection, a rapid method has been developed to detect and clone amplified DNA sequences from cytologically-recognizable markers such as dmin or hsrs (Guan et al., 1994). By combining microdissection and FISH, this amplification probe makes readily available a means of rapid pretreatment analysis on prostate biopsy core specimens that subsequently can be used for routine histopathologic examination.

Because the particular 8q24 region of human chromosome 8 has been in general described as important in human cancers, the particular probes identified by the present inventors within the human chromosome 8q24 region are expected to provide a very powerful molecular tool for screening a patient sample for progression of human prostate cancer through the detection of particular genetic lesions within this small region.

In particular embodiments, the present invention demonstrates that the genetic amplification of a particular region (8q24.1–24.2) is detectable according to the herein described method and this amplification correlates with the presence of human prostate cancer. This genetic amplification has been found to exist in samples obtained from patients with established prostate cancer.

One object of the present invention is to provide probes for the identification of this gene amplification and to determine the involvement of different mutations in the development and progression of human prostate cancer. Another object of the present invention is to provide probes that are useful in identifying the particular 8q24 region of chromosome 8, which has inherently a number of utilities. Among these is the practical utility for use in genetic patient sample evaluation to determine whether dmins hybridizable to this probe exist in a patient sample, which are indicative of metastastic progression.

Such information is particularly useful in a clinical setting to permit the clinician to identify the presence of chromosome 8 in the sample, and to particularly determine whether or not the particular region within chromosome 8, (8q24.1–24.2) exists in single or multiple copies.

In other embodiments, the present invention illustrates the usefulness of chromosome microdissection in the analysis of dosage abnormality of chromosome changes in prostate cancers. A common region of DNA sequence amplification (8q24) has been documented in a subset of patients which may have a propensity for disease progression. Recurrent patient samples were examined, and a high incidence of 8q gain was demonstrated, indicating a less favorable prognosis because of this genetic alteration.

While it is contemplated that any tissue sample may be employed in the analysis of a sample DNA, the most preferred type of tissue using the aforedescribed method is blood, prostate tissue, or prostate tumor tissue. However, the inventors contemplate that the method may also be used with other cell types, including a variety of solid tumor samples or even blood samples. Most preferred of these is prostate tumor tissue. Where a sample RNA is desired, the most preferred tissue for use is prostate tissue. However, where sample DNA is desired, a blood sample from the patient is most particularly preferred as the tissue of choice.

In general terms, the invention relates to a method of determining prostate cancer metastasis progression by detecting amplification using a probe derived from double minute (dmin) chromosomes from the 8q24 region of chromosome 8. Surprisingly, using this method, a region of amplification on chromosome 8 (HSA8q24.1–q24.2), was found from the dmin of a patient with PCA (By conventional nomenclature HSA refers to a Homo sapiens autosome).

A novel mixed oligonucleotide family of probes was obtained from a dmin identified as PRO39 using the degenerate sequence primer of SEQ ID NO:1. Amplification of this 8q24-specific DNA region generated a mixed probe which was used to determine the occurrence of gene amplification in other patient specimens. Surprisingly a unique DNA segment of this probe was further localized to the 8q24.1–24.2 region, and was shown to be diagnostic for metastatic progression of prostate cancer. It is quite likely that one or more unique members of this probe family will be useful for the isolation of particular subregions of 8q24.1–24.2, and the identification of specific gene(s) associated with prostate cancer. Such unique probes will provide the basis for diagnostic kits identifying metastatic tumor progression in these patients.

The inventors are the first to show that a probe hybridizable to a region of chromosome 8 (8q24.1–24.2) can be used as a prognostic tool for prostate cancer. Surprisingly, increased copy number in this region of chromosome 8 is indicative of metastatic prostate cancer progression.

BRIEF DESCRIPTION OF THE DRAWINGS

FIG. 2B shows the identical partial metaphase following FISH identifying the normal chromosomal locus of the dissected dmin from PRO39 as 8q24.1 (arrow).

DETAILED DESCRIPTION OF THE PREFERRED EMBODIMENTS

Molecular analyses allow one to determine genetic lesions occurring early in the development of tumors. The present invention provides clones from human chromosome 8q24, a region which contains genes involved in tumorigenesis or progression.

B. Nucleic Acid Embodiments

The DNA sequences disclosed herein find utility as probes or primers in nucleic acid hybridization embodiments. As such, it is contemplated that oligonucleotide fragments of sufficient length to provide specific hybridization to a DNA tissue sample, such as a fragment of between about 10 nucleotides to about 20, or to about 30 nucleotides, will find particular utility. Longer sequences, e.g., 40, 50, 100 to 500, even up to full length, are even more preferred for certain embodiments. The ability of such nucleic acid probes to specifically hybridize to tissue-specific sequences will enable them to be of use in a variety of embodiments.

For example, the probes can be used in a variety of assays for detecting the presence of complementary sequences in a given tissue sample. However, other uses are envisioned, including the use of the sequence information for the preparation of mutant species primers, or primers for use in preparing other genetic constructions.

Nucleic acid molecules having stretches of 10, 20, 30, 50, 60, 65 or even up to and including 100 to 500 nucleotides or so, and those complementary to SEQ ID NO: 1 may also have utility as hybridization probes. These probes will be useful in a variety of hybridization embodiments, such as Southern and Northern blotting in connection with analyzing tissue-specific structural or regulatory genes in tissue samples. The total size of fragment, as well as the size of the complementary stretches, will ultimately depend on the intended use or application of the particular nucleic acid segment. Smaller fragments will generally find use in hybridization embodiments, wherein the length of the complementary region may be varied, such as between about 10 and about 100 nucleotides, or even full length according to the complementary sequences one wishes to detect.

The use of a hybridization probe of about 20 nucleotides in length allows the formation of a duplex molecule that is both stable and selective. Molecules having complementary sequences over stretches greater than 20 bases in length are generally preferred, though, in order to increase stability and selectivity of the hybrid, and thereby improve the quality and degree of particular hybrid molecules obtained. One will generally prefer to design nucleic acid molecules having gene-complementary stretches of 20 to 30 nucleotides, or even longer where desired. Such fragments may be readily prepared by, for example, directly synthesizing the fragment by chemical means, by application of nucleic acid reproduction technology, such as the PCR™ technology with two priming oligonucleotides of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of tissue-specific genes or cDNAs or to provide primers for amplification of DNA or cDNA from tissues. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02M to about 0.15M NaCl at temperatures of about 50° C. to about 70° C. Such selective conditions tolerate little, if any, mismatch between the probe and the template or target strand, and would be particularly suitable for isolating tissue-specific genes.

Of course, for some applications, for example, where one desires to prepare mutants employing a mutant primer strand hybridized to an underlying template or where one seeks to isolate tissue-specific-encoding sequences from related species, functional equivalents, or the like, less stringent hybridization conditions will typically be needed in order to allow formation of the heteroduplex. In these circumstances, one may desire to employ conditions such as about 0.15M to about 0.9M salt, at temperatures ranging from about 20° C. to about 55° C. Cross-hybridizing species can thereby be readily identified as positively hybridizing signals with respect to control hybridizations.

In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as in PCR™ for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove non-specifically bound probe molecules, specific hybridization is detected, or even quantified, by means of the label.

Longer DNA segments will often find particular utility in the recombinant production of peptides or proteins. DNA segments which encode peptide antigens from about 15 to about 50 amino acids in length, or more preferably, from about 15 to about 30 amino acids in length are contemplated to be particularly useful, as are DNA segments encoding entire tissue-specific proteins. DNA segments encoding peptides will generally have a minimum coding length in the order of about 45 to about 150, or to about 90 nucleotides.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular probes disclosed herein and particularly is intended to encompass at least nucleic acid sequences that are hybridizable to these sequences or are functional sequence analogs of these sequences. DNA segments prepared in accordance with the present invention may encode biologically functional proteins or peptides. Functionally equivalent proteins or peptides having variant amino acid sequences may arise as a consequence of codon redundancy and functional equivalency which are known to occur naturally within nucleic acid sequences and the proteins thus encoded. Functionally equivalent proteins or peptides may alternatively be constructed via the application of recombinant DNA technology, in which changes in the protein structure may be engineered, based on considerations of the properties of the amino acids being exchanged.

DNA segments encoding a tissue-specific gene may be introduced into recombinant host cells and employed for expressing a tissue-specific structural or regulatory protein. Alternatively, through the application of genetic engineering techniques, subportions or derivatives of selected tissue-specific genes may be employed. Upstream regions containing tissue-specific regulatory regions such as promoter regions may be isolated and subsequently employed for tissue-specific expression.

Promoters and enhancers control the transcription of protein encoding genes in mammalian cells and, in effect, allow tissues to be differentiated from each other. The identification of tissue-specific-encoding sequences of the present invention allows the isolation of tissue-specific promoters and their use in targeted gene expression.

Promoters are composed of multiple genetic elements. The cellular machinery is able to gather and integrate the regulatory information conveyed by each element, allowing different genes to evolve distinct, often complex patterns of transcriptional regulation.

The term promoter refers to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies have shown that promoters are composed of discrete functional modules, each consisting of approximately 7–20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation of transcription.

Additional promoter elements regulate the frequency of transcriptional initiation. Typically, these are located in the region 30–110 bp upstream of the start site, although a number of promoters contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either cooperatively or independently to activate transcription.

C. Biological Functional Equivalents

As mentioned above, modification and changes may be made in the structure of a gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by change the codons of the DNA sequence, according to the following data (Table 1)

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982,

TABLE 1

| Amino Acids | | | Codons | | | | | |
| --- | --- | --- | --- | --- | --- | --- | --- | --- |
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | | incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outline above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

D. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired protein. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected gene using site-directed mutagenesis is provided as a means of producing potentially useful species and is not meant to be limiting as there are other ways in which sequence variants of genes may be obtained. For example, recombinant vectors encoding the desired gene may be treated with mutagenic agents, such as hydroxylamine, to obtain sequence variants.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/ biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

Tissue-specific sequences of the present invention may be used to isolate tissue-specific promoters by hybridization of the cDNA sequences provided to a genomic clone so that flanking sequences may be obtained. Upstream (i.e., 5') flanking sequences may be constructed next to a reporter gene to assay for the expression of the protein product of the reporter gene and therefore, assay for promoter activity. A series of such upstream sequences having promoter activity may define a tissue specific promoter.

E. dmins as a Target for Chromosome Microdissection

The presence of dmin in metaphase spreads from short-term prostate cultures provides a target for the technique of chromosome microdissection. This procedure uses a glass microneedle to dissect (under the microscope) dmins and amplify this minute amount of DNA via the polymerase chain reaction (PCR™) (Meltzer et al., 1992). The product is then hybridized to normal banded lymphocyte metaphase chromosomes to determine the chromosomal location of the amplified genes (Zhang et al., 1993; Guan et al., 1994).

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the particular embodiments which are disclosed and still obtain a like or similar result without departing from the spirit and scope of the invention.

F. MATERIALS AND METHODS

1. Surgical Specimens

Tissue from primary disease specimens for FISH or microdissection was obtained from patients at the Mayo Clinic, University of Texas Health Science Center-San Antonio or Johns Hopkins University undergoing radical prostatectomy. All samples were obtained prior to administration of any hormonal therapy, and all as part of their regular clinical care. All recurrent specimens came from Tampere University Hospital following transurethral resections of patients who had responded favorably to endocrine therapy (orchiectomy-6 cases; LHRH-agonist-2 cases; estrogen-1 case), but later showed symptoms of local recurrence.

2. Preparation of Metaphase Chromosomes for Microdissection

In order to obtain metaphase chromosomes for microdissection, cells were analyzed from a short term culture of a primary tumor specimen (PRO-39) and from an established prostate cancer cell line (MPC-3).

Primary tumor tissue was obtained at the time of radical prostatectomy from case PRO-39 and a portion of the tumor was used for determination of histology and standard pathology. The specimen was obtained from a 63-year-old male. The pathological findings concluded 45% of the prostate gland was involved by moderately to poorly differentiated adenocarcinoma, Gleason's grade 8/10 (5+3/10) (Table 1) as: 1) poorly differentiated adenocarcinoma (primary pattern 5 in Gleason's grading system), 2) moderately differentiated adenocarcinoma (secondary pattern 3 in Gleason's grading system).

Only 1 of 13 lymph nodes examined demonstrated metastatic adenocarcinoma. Prostate tumor chips were transported in McCoy's media with 10% fetal bovine serum (FBS), 2% HEPES buffer, Penicillin/Streptomycin 5,000 units/ml, and sodium pyruvate, 2 mM. Tissue for cytogenetic analysis was minced into 1–2 mm$^3$ fragments then forced through a 100 mesh sieve. A single-cell suspension was made bypassing cells through a 22.5-gauge needle. Cells were centrifuged and washed, then resuspended in McCoy's 5A medium as described above.

Cells were treated with colcimid (0.12 ug/ml) for 60 minutes. Cells were removed from the flask using 0.25% trypsin/ml 1 mM EDTA, resuspended in 0.075M KCl at room temperature for 20 min, centrifuged and subsequently fixed in 3:1 (methanol:glacial acetic acid). After overnight fixation at −20° C. the cells are refixed in fresh fixative and metaphase spreads were stained with Wright's stain as previously described (Trent and Thompson, 1987).

The MPC-3 prostate tumor cell line (previously reported to contain dmins and possess c-myc amplification [Ware et al., 1982; Fukumoto et al., 1988]), was grown in RPMI with 10% FBS and glutamine. MCP-3 cells were exposed to colcimed, harvested, fixed, and prepared on slides as described above.

4. Microdissection and Amplification of dmin DNA

The microdissection and PCR™ amplification of dissected dmin DNA was performed essentially as previously described (Guan et al., 1993). Briefly, microdissection was performed using glass microneedles controlled by a micromanipulator attached to an inverted microscope. The target region of dissection in both the primary specimen and the prostate cell line were 3–5 of dmins. The dissected dmin fragments (which adhere to the microneedle) were transferred to a 5 μl collection drop and amplified using previously published methods for degenerate oligonucleotide primed PCR™.

Basically, dmins were transferred to 0.5 ml PCR™ tubes following the procedure of Zhang et al. (1992; 1993) where a pre-amplification protocol for eight cycles (93° C.) for 1 min; 30° C. for 4 min [heat-sensitive T7 DNA polymerase (Sequenase™) is added manually each cycle]; 37° C. for 2.5 min) followed by a standard PCR™ reaction with Taq polymerase (Perkin/Elmer Cetus, Emeryville, Calif.) (94° C. for 1 min; 56° C. for 2 min; 72° C. for 2.5 min) for 30 cycles. From this PCR™ reaction, 2 μl was used in a secondary PCR™ reaction with equimolar amounts of biotin-dUTP and dTTP. The PCR™ conditions were identical to the standard Taq polymerase reaction described above. This PCR™ reaction product was used as the labeled probe in the mapping and related studies.

The amplified microdissected DNA was labeled with biotin-11-dUTP in a secondary PCR™ reaction and the products purified and used for FISH. Hybridization of the FISH probes followed previously described procedures (Pinkel et al., 1986) and provided unequivocal evidence of hybridization to the dmin DNA.

Microslides with metaphase spreads of the desired target cells were denatured, dehydrated and hybridized with the labeled dmin probe mixture. After an overnight incubation the slides were washed to remove non-hybridized probe. Probe detection was accomplished by first incubating the slides with 5 ug ml-1 avidin-FITC (fluorescein isothiocyanate) (Vector Laboratories, Burlingame, Calif.). The slide was washed and the signal amplified by incubating in 5 μg ml-1 biotinylated anti-avidin (Vector) followed by washing and reincubating with avidin-FITC. Chromosomes were counterstained with propidium iodide (0.2 ng/ml), and an antifade solution and coverslips were added.

From the chromosomal map position of the dmin clones, it was possible to determine if the amplified dmins consisted of uncharacterized novel amplicons (amplified regions) or known amplified genes (e.g., c-Myc or erb-B2). With probes derived from PCA dmins it was possible to assess the significance of each amplicon prospectively by using FISH on fresh tumor touch preps. Following identification of tumor in resected tissue (by frozen section and hematoxylin and eosin staining), touch preps were collected onto coated slides and processed for FISH. Slides were analyzed by FISH to detect gene amplification.

5. FISH Analysis of Tumor Tissue Specimens

Dual color hybridizations with a directly-labeled probe for the centromere of chromosome 8 (Spectrum Green CEP-8, VYSIS, Framingham, Mass.) and the directly-labeled Spectrum Orange 8q24 probe were performed on prostate tumor touch preparations as previously described (Pearsons et al., 1993). Post-hybridization conditions and methods of microscopic analysis have also been previously reported (Pearsons et al., 1993).

For each batch of hybridizations a negative control (benign prostate tissue at Mayo, peripheral blood lymphocytes at Hopkins) was hybridized and scanned to demonstrate successful and appropriate normal hybridization signals. In the normal control and in the apparently 8q24 non-amplified tumor cases one small, distinct orange-red signal (from the 8q24 probe) was observed to be associated with each of the larger green signals (the CEP 8 probe) in ≧92% of cells.

For each batch of hybridizations a positive control (the MPC-3 cancer cell line) was also hybridized and scanned to demonstrate successful and appropriate amplification signals. Amplification of 8q24 was defined by multiple (often diffuse) orange-red signals associated with one or more of the green signals or as large orange-red signal domains within a nucleus. The observation of 4 8q24 signals and 2 CEP8 signals (e.g., four copies of the 8q-arm or 8q24 and two copies of the chromosome 8 centromere) was not defined as amplification. Whenever possible, both 8 chromosome hybridization and the 8q Micro-FISH probe were simultaneously assayed.

For each of the prostate tumors studies, the entire hybridization site (22×22 mm) was analyzed. All nuclei encountered while scanning were carefully evaluated for the presence of amplification. If amplifications were observed following this complete scan, 200–250 random nuclei were scored and the percent nuclei demonstrating amplification was recorded (Table 1).

6. Comparative Genomic Hybridization

CGH was performed on three prostate cell lines (du145, LNCap, and PC-3) and 9 recurrent tumors using directly fluorochrome-conjugated DNAs as previously described (Kallioniemi et al., 1992; Kallioniemi et al., 1994). Briefly, normal lymphocyte metaphase preparations were denaturated at 72°–74° C. for 3 min in 70% formamide/2× SSC (pH 7), and dehydrated in a series of 70%, 85% and 100% ethanol followed by proteinase K (0.1 mg/ml in 20 mM Tris-HCl, 2 mM CaCl$_2$, pH 7.5) treatment at room temperature and a second round of dehydration as described above.

DNA isolated from tumors was labeled with FITC-dUTP (DuPont, Boston, Mass.) and normal male DNA with TexasRed-dUTP (DuPont) using nick translation. Hybridization mixture containing 400 ng labeled tumor and normal DNA and 10 mg unlabeled Cot-1 DNA (Gibco BRL, Gaithersburg, Md.) in 10 ml of 50% formamide/10% dextran sulphate/2× SSC was denaturated and applied on normal lymphocyte metaphase preparations. The hybridization was done under a coverslip in a humid chamber at 37° C. for 48 hours. After hybridization, the slides were washed three times in 50% formamide/2× SSC (pH 7), twice in 2× SSC and once in 0.1× SSC at 45° C. for 10 min each followed by 2× SSC, 0.1M NaH$_2$PO$_4$-0.1M Na$_2$HPO$_4$-0.1% Nonidet P-40™ (pH 8) and distilled water at room temperature for 10 min each. The slides were then counterstained with 4,6-diamidino-2-phenylindole (DAPI, 0.1 mg/ml) in an antifade solution. Hybridizations of FITC-labeled normal female DNA with TexasRed-labeled normal male DNA were used as controls.

7. Digital Image Analysis

Detection of relative DNA sequence copy number changes in chromosome 8 was accomplished by analyzing hybridization intensities of tumor and normal DNAs along chromosome 8 in metaphase spreads using a digital image analysis system as previously described (Kallioniemi et al., 1994). Three single-color images (matching DAPI, FITC, and Texas Red fluorescence) were collected from 4–5 metaphases from each hybridization using a Nikon SA epifluorescence microscope (Nikon Corporation, Tokyo, Japan) and a Xillix CCD camera (Xillix Technologies Corp, Vancouver, BC, Canada) interfaced to a Sun LX workstation (Sun Microsystems Computer Corp, Mountain View, Calif.). After background subtraction, the green and red fluorescence intensities from $P_{ter}$ to $q_{ter}$ and the ratio of the two were calculated. The absolute fluorescence intensities were normalized for each metaphase spread so that the average green to red ratio of all chromosome objects in the metaphase was 1.0. The final result was plotted as a mean green to red ratio profile and its ±1 SD from $P_{ter}$ to $q_{ter}$ along chromosome 8 obtained from 4–8 chromosome homologues.

G. RESULTS

The results of the present invention demonstrated that 4 of 44 primary prostate cancers and 8 of 9 recurrent prostate tumors had evidence of DNA copy number gains of 8q. For the primary tumors, gain of chromosomal material at 8q24 was specifically identified by FISH, while in recurrent tumors CGH recognized 8q gain. By CGH whole arm gain was observed in 7 of 9 tumors, with one case demonstrating amplification restricted to 8q24-qter. The commonly amplified region between all cancers was 8q24, and while in some tumors the degree of multiplication and size of the region involved may indicate a gross chromosomal change such as an isochromosome of 8q, clear documentation of gene amplification was observed in numerous cases.

The data from both chromosome microdissection and CGH provides evidence for a common region of amplification spanning several megabases of DNA. The size of this segment is sufficiently large to contain several dozen genes and one or more of these may contribute to the growth advantage during development and reprogression of prostate tumors.

Of interest, the gain of 8q recognized by standard cytogenetic analysis has implicated its involvement in many other cancers including acute nonlymphocytic leukemia, hepatocellular carcinoma, renal cell cancer, gastric cancer, uveal melanoma, myelodysplastic syndrome, and colon cancer and may explain a broader role for 8q alteration in carcinogenesis. In this regard there is a strong candidate gene located within 8q24 which may be the target of the 8q amplification: c-myc. Although amplification of c-myc has not previously been reported in primary prostate malignancies, evidence for the overexpression of c-myc as a possible maker of poor prognosis in prostate cancer has previously appeared (Fleming et al., 1986).

1. Identification of Gene Amplification in Prostate Cells by Chromosome Microdissection Using a strategy to identify and characterize gene amplification by targeting dmin or hsrs for microdissection (Zhang et al., 1993 Guan et al., 1994), the results of microdissecting dmin from two prostate cancers identified a common origin of amplified DNA in both cases. Using the microdissection probe, the inventors were able to test interphase tumor cells from patient samples.

Figure 1A:
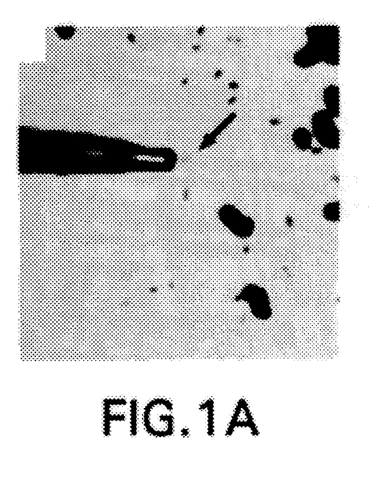
FIG. 1A. Utilization of chromosome microdissection to elucidate the chromosomal composition of double minutes from a primary prostate cancer metaphase spread. Microdissection of a single double minute (dmin, arrow) from case PRO39.
Figure 1B:
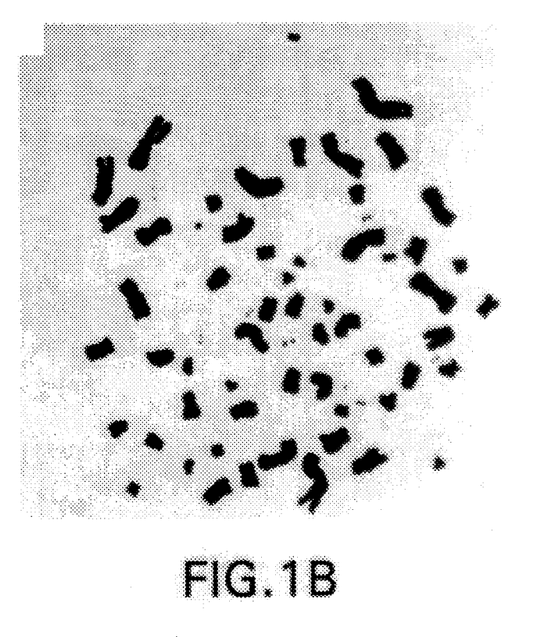
FIG. 1B. After microdissection of dmin, PCR™ amplification, and biotin labeling of the dissected DNA, the PCR™ product is purified and hybridized by FISH back to the dmin to confirm that the dissection product hybridizes to the hsr. The identical metaphase tumor cell from case PRO39 is shown following Giemsa staining.

Dmin from the primary tumor case Pro-39 and from the MPC-3 prostate cancer cell line were microdissected (FIG. 1A) and directly amplified in vitro by PCR™. The PCR™ amplified DNA sequences were then secondarily labeled with a fluorochrome and used for FISH against metaphase tumor cells from which the dissections were derived (FIG. 1B). The results of FISH to both dmin-bearing tumor cell metaphases clearly documented hybridization to the dmin confirming the presence of DNA sequence amplification (FIG. 1C).

Figure 2A:
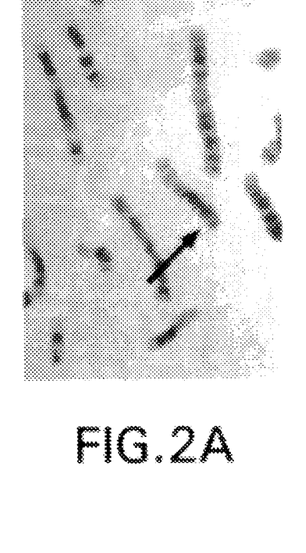
FIG. 2A. Chromosomal localization of amplified dmin DNA from the primary prostate cancer PRO39 by FISH. Shown is the G-banded normal partial metaphase with arrow to region of hybridization on chromosome 8.
Figure 2B:
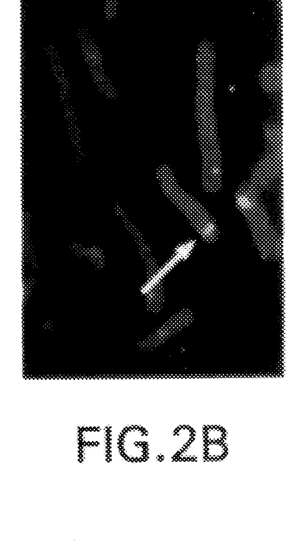
FIG. 2B. Chromosomal localization of amplified dmin DNA from the primary prostate cancer PRO39. The G-banded normal partial metaphase with arrow to region of hybridization on chromosome 8 in FIG. 2A is shown following FISH identifying the normal chromosomal locus of the dissected dmin from PRO39 as 8q24.1 (arrow).
Figure 2C:
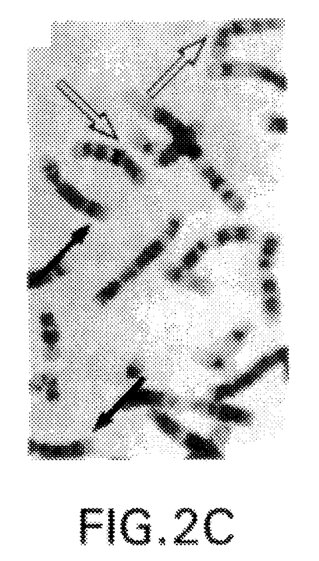
FIG. 2C. Chromosomal localization of amplified dmin DNA from the prostate cancer cell line PC-3 by FISH. Shown is the G-banded normal partial metaphase with solid arrow to the region of hybridization on chromosome 8, and the open arrow to the region of hybridization on chromosome 10. The identical partial metaphase following FISH identifying the normal chromosomal locus of the dissected dmin from PC-3 as 8q24 and 10cen is shown in FIG. 2D.
Figure 2D:
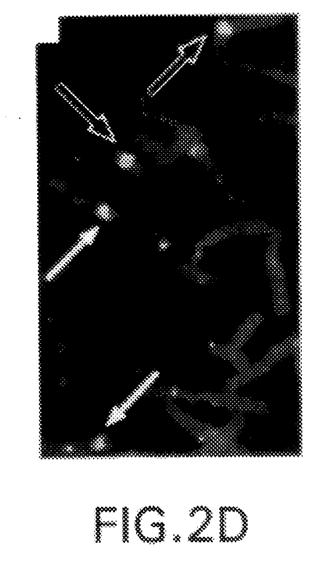
FIG. 2D. Chromosomal localization of amplified dmin DNA from the prostate cancer cell line PC-3 by FISH. The G-banded normal partial metaphase from FIG. 2C is shown following FISH identifying the normal chromosomal locus of the dissected dmin from PC-3 as 8q24 and 10cen.

Subsequently, the dmin microdissection probe was used to hybridize against metaphase spreads from normal peripheral blood lymphocytes in order to identify the chromosomal loci of the amplified DNA sequences encoded within the dmin (FIG. 2A, FIG. 2B). The origin of the amplified DNA within Pro-39 dmin was shown to encompass band-region 8q24 (FIG. 2C). The dissected dmin DNA from MPC-3 was shown to hybridize to two different band regions, 8q24 and 10cen (FIG. 2C, FIG. 2D).

The Pro-39 microdissection probe was then hybridized to MPC-3 metaphases and hybridization was visible on 100% of the recognizable dmin. A biotin-labeled c-MYC cosmid was then hybridized to mitoses from PRO-39, PC-3 and MPC-3. In all three cases, c-MYC sequences were shown to hybridize to all dmin (FIG. 1C, inset).

Figure 1C:
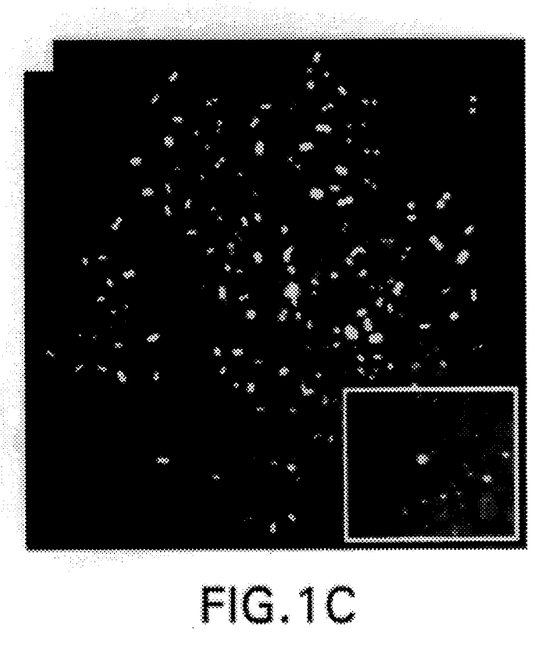
FIG. 1C. Shown is the metaphase tumor cell from case PRO39 following FISH. Note the FISH probe clearly identifies multiple dmin not recognized by conventional Giemsa staining (FIG. 1B). Inset, FISH of a biotin labeled c-MYC cosmid to metaphase cell from PRO39 indicating hybridization to dmin.

The presence of c-MYC sequences within dmin from the Pro-39 tumor metaphases and the PC-3 and MPC-3 cell lines was directly demonstrated using FISH (FIG. 1C, inset). Although the c-MYC gene is encoded within the dmin, previous estimation of the size of the c-MYC amplicon (90–300 kb [Kinzler et al., 1986]) would account for <<10% of the total dmin DNA. Although it is likely that c-MYC is the target of the amplification of 8q sequences, there may be other gene(s) involved in the apparent physiologic effects of amplification of this chromosomal region.

2. FISH Analysis of Prostate Tumor Specimens

Based upon the identification of a commonly amplified band-region (8q24), dual-color FISH [using a directly labeled probe for the centromere of 8 (labeled green) and the dissected band-region 8q24 (labeled orange/red)] was performed on touch preparations from the tumors of 44 patients with prostate cancer. Table 2 summarizes the clinical information and amplification status of 8q24 amplification of all 44 patients. Within this unselected patient population 4/44 (9%) were scored as amplified [defined as multiple diffuse (orange/red) signals associated with one or more green signals within a nucleus] (FIG. 3A, FIG. 3B, FIG. 3C, FIG. 3D). Of interest, 4/44 patients were also node positive at the time of initial diagnosis, and in 3/4 node-positive patients, 8q24 amplification was observed.

Utilization of fresh tumor preparations for FISH has routinely allowed >500 non-overlapping intact nuclei to be examined by FISH from the same biopsy specimen used for histologic evaluation. The use of a microdissection probe for 8q24 provided FISH results equivalent to those for the more frequently studied centromeric probes. This study clearly documents chromosome 8 gain as a frequent change in prostate cancer progression.

Importantly, the clinical history of all patients was unknown to the laboratory performing the FISH studies. Also, each case amplified for 8q24 was re-evaluated to confirm the presence of amplified cells.

TABLE 2

| Patient # | Inst.[1] | CS[2] | Pre-Op PSA Value | Post-Op Pathol. Staging | Gleason's Score 1° | Gleason's Score 2° | Differentiation (Poor, Med, Well) (Mayo 3, 2, 1) | Ploidy FCM | S2q Probe Results | Tumor Size (cm) |
|---|---|---|---|---|---|---|---|---|---|---|
| 24 | Mayo | C | 13.40 | 3a-0-0 | 2 | 3 | 2 | diploid | neg | 4.2.2 |
| 32 | Mayo | B | 1.00 | 2a-0-0 | 2 | 3 | 2 | diploid | neg | 2 × 1 × 1 |
| 28 | Mayo | C | 6.20 | 3a-0-0 | 3 | 4 | 3 | diploid | neg | 2 × 1 × 1 |
| 11 | Mayo | C | 4.00 | 3a-0-0 | 3 | 3 | 2 | diploid | neg | 2.5 × 1.7 × 3.5 |
| 13 | Mayo | B | 5.60 | 2c-0-0 | 3 | 4 | 3 | diploid | neg | 2 × 1.5 × 0.5 |
| 5 | Mayo | B | 7.80 | 2c-0-0 | 3 | 2 | 2 | diploid | neg | 3 × 3 × 1 |
| 16 | Mayo | C | 4.10 | 3a-0-0 | 3 | 3 | 2 | diploid | neg | 2.4 × 1.8 × 1 |
| 1 | Mayo | B | 19.70 | 2c-0-0 | 3 | 3 | 3 | diploid | neg | 2 × 2 × 1 |
| 17 | Mayo | C | 4.20 | 3c-0-0 | 3 | 2 | 2 | diploid | neg | 2.5 × 2.5 × 1.3 |
| 51 | Mayo | B | 11.70 | 2c-0-0 | 2 | 3 | 2 | diploid | neg | 4.2 × 4 × 3.9 |
| 10 | Mayo | C | none | 33a-0-0 | 3 | 3 | 3 | diploid | neg | 1.5 × 1.5 × 1 |
| 20 | Mayo | C | 22.60 | 3b-0-0 | 3 | 3 | 3 | diploid | neg | 3.5 × 3 × 1.3 |
| 6 | Mayo | B | 6.20 | 2c-0-0 | 1 | 2 | 2 | diploid | neg | 0.8 |
| 2 | Mayo | C | 8.50 | 3a-0-0 | 3 | 3 | 3 | tetraploid | neg | 2.5 × 2 × 1 |
| 34 | Mayo | C | 6.10 | 3-0-0 | 3 | 4 | 3 | diploid | neg | 2.3 × 1.8 × 0.8 |
| 23 | Mayo | C | 3.90 | 3b-0-0 | 3 | 3 | 3 | diploid | neg | 4 × 2.8 × 1.1 |
| 39 | Mayo | B | 4.60 | 2c-0-0 | 3 | 3 | 2 | tetraploid | neg | 2 × 2 × 1 |
| 31 | Mayo | C | 5.70 | 3a-0-0 | 1 | 3 | 2 | tetraploid | neg | 2.2 × 1.7 × 0. |
| 9 | Mayo | B | 5.70 | 2b-0-0 | 3 | 5 | 3 | tetraploid | neg | 2 × 2 × 1 |
| 8 | Mayo | C | 3.10 | 3a-0-0 | 3 | 3 | 3 | diploid | neg | 1.5 × 1 × 0.8 |
| 18 | Mayo | C | 35.60 | 2b-0-0 | 3 | 2 | 3 | tetraploid | neg | 2.5 × 2 × 1.5 |
| 19 | Mayo | B | 4.90 | 2b-0-0 | 3 | 4 | 3 | tetraploid | neg | 2 × 2 × 1 |
| 21 | Mayo | C | 19.20 | 3a-0-0 | 3 | 4 | 3 | tetraploid | neg | 2 × 1.5 × 1.5 |
| 25 | Mayo | C | 26.60 | 3c-0-0 | 3 | 4 | 3 | tetraploid | neg | 4 × 3.5 × 2.5 |
| 33 | Mayo | C | 4.50 | 3c-1-0 | 3 | 3 | 3 | tetraploid | amplified | 4.5 × 3 × 2 |

TABLE 2-continued

| Patient # | Inst.[1] | CS[2] | Pre-Op PSA Value | Post-Op Pathol. Staging | Gleason's Score 1° | Gleason's Score 2° | Differentiation (Poor, Med, Well) (Mayo 3, 2, 1) | Ploidy FCM | S2q Probe Results | Tumor Size (cm) |
|---|---|---|---|---|---|---|---|---|---|---|
| 35 | Mayo | C | 16.70 | 3c-0-0 | 2 | 4 | 2 | diploid | neg | 3.5 × 2 × 1.2 |
| 37 | Mayo | C | 5.70 | 3c-0-0 | 3 | 4 | 3 | aneuploid | amplified | 4 × 3.5 × 3 |
| 43 | Mayo | C | 9.30 | 3c-0-0 | 3 | 4 | 3 | tetraploid | neg | 2.5 × 2 × 1.3 |
| 46 | Mayo | C | 9.30 | 3-0-0 | 3 | 3 | 3 | tetraploid | neg | 5 × 3 × 1.5 |
| 48 | Mayo | C | 28.30 | 4a-0-0 | 3 | 3 | 3 | aneuploid | CEP8/8q24 <1 | 4 × 4 × 3.3 |
| 53 | Mayo | C | 8.80 | 3c-0-0 | 3 | 3 | 3 | diploid | neg | 2.5 × 2.2 × 1.5 |
| 94-084 | Hopkins | B | 22.50 | 3c-1-0 | 4 | 4 | NA* | aneuploid | amplified (84) | NA |
| 94-007 | Hopkins | C | 7.60 | 3a-0-0 | 3 | 3 | NA | ND | neg | NA |
| 94-002 | Hopkins | B | 3.70 | 2b-0-0 | 3 | 3 | NA | ND | neg | NA |
| 94-008 | Hopkins | C | 8.90 | 2b-0-0 | 3 | 4 | NA | aneuploid | neg | NA |
| 94-027 | Hopkins | C | 10.10 | 2a-0-0 | 3 | 3 | NA | ND | neg | NA |
| 94-089 | Hopkins | C | 1.00 | 2a-0-0 | 3 | 4 | NA | diploid | neg | NA |
| 94-044 | Hopkins | C | 6.40 | 2a-0-0 | 4 | 3 | NA | diploid | neg | NA |
| 94-024 | Hopkins | C | 4.30 | 2c-0-0 | 4 | 4 | NA | diploid | neg | NA |
| 94-020 | Hopkins | C | 21.80 | 2a-0-0 | 3 | 3 | NA | aneuploid | neg | NA |
| 94-049 | Hopkins | C | 12.80 | 2b-0-0 | 3 | 3 | NA | diploid | neg | NA |
| PRO-39 | UTSA | B | 31.0 | 3b-1-0 | 5 | 3 | 3 | NA | amplified | NA |

[1]Institution;
[2]Clinical Stage

3. CGH Analysis of Recurrent Prostate Tumor Tissue

Figure 3A:
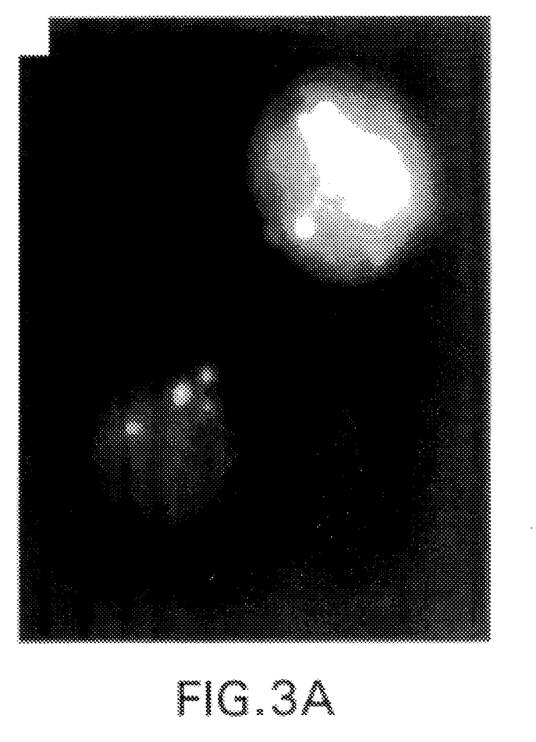
FIG. 3A. FISH analysis indicating DNA sequence copy number increase for 8q in primary prostate cancer. Shown is the FISH with a centromere probe for chromosome 8 (arrows) and a microdissection probe for 8q24 (isolated from PRO39 dmin), on a touch prep from normal prostate cells demonstrating two signals for each probe in interphase nuclei.
Figure 3B:
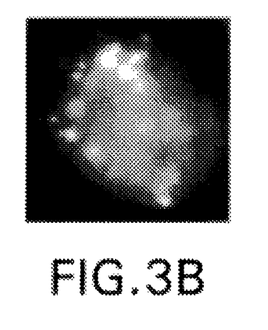
FIG. 3B. FISH with a centromere probe for chromosome 8 (arrows) and the microdissection probe for 8q24 (open arrows) to interphase nuclei from the amplified prostate case 33.
Figure 3C:
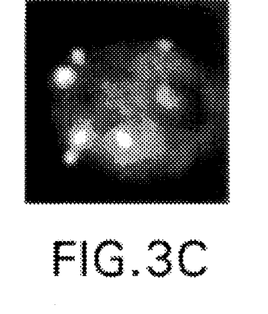
FIG. 3C. Compared to FIG. 3B, note that the prostate cancer cells show gains of 8q24 signals (open arrows) relative to the 8 centromere (arrows) consistent with amplification of DNA sequences in this region.
Figure 3D:
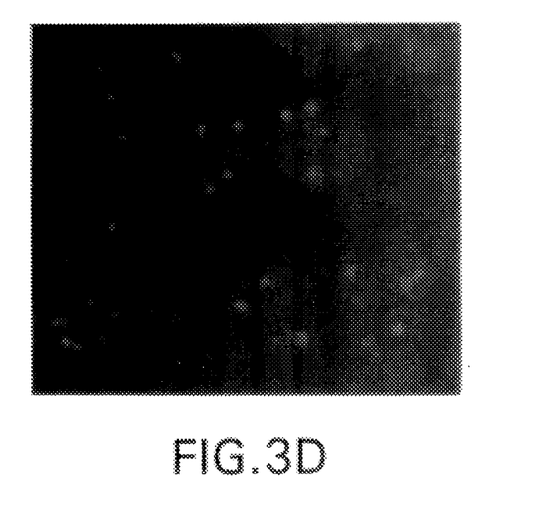
FIG. 3D. FISH using the microdissection probe for 8q24 hybridized to interphase nuclei from the amplified prostate case 94-084, again demonstrating multiple copies of 8q24.
Figure 3E:
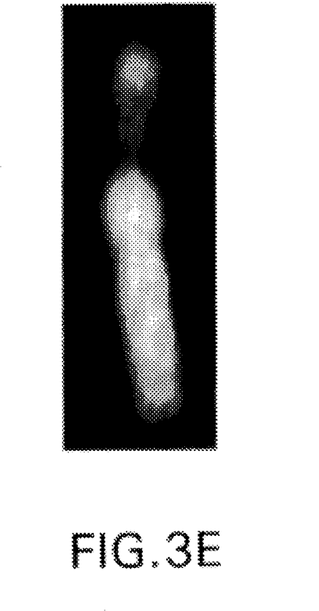
FIG. 3E. Comparative Genomic Hybridization analysis indicating DNA sequence copy number increase for 8q in a case of recurrent prostate cancer. Shown is a metaphase chromosome 8 from normal donor following CGH with DNA from a recurrent prostate cancer.
Figure 3F:
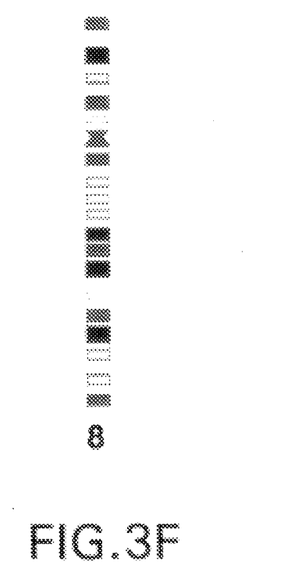
FIG. 3F. G-banded ideogram from chromosome 8.
Figure 3G:
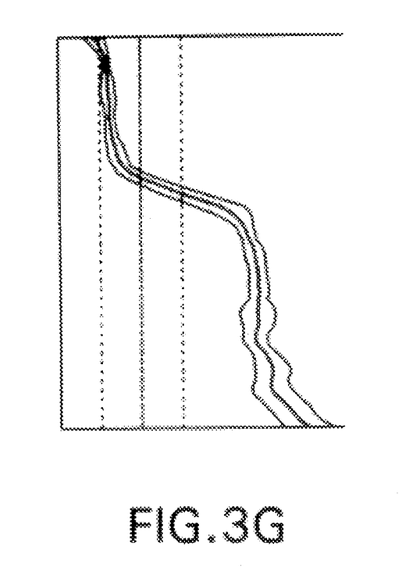
FIG. 3G. Green:red-fluorescence intensity ratio (from FIG. 3E) for chromosome 8. The ratio is derived from several metaphase spreads hybridized to the same tumor sample and clearly indicates an increase in 8q copy number in this cancer.

CGH was used to delineate the frequency of 8q copy number gain from three cell lines (du145, LNCap, and PC-3), and nine cases of recurrent prostate cancer. No copy number changes at 8q were found in either the du145 or LNCap cell lines. In contrast, the PC-3 cell line showed gain of 8q13-qter and loss of 8pter-q12 (FIG. 3E, FIG. 3F, FIG. 3G).

This report focuses exclusively on the identification of increased copy number on 8q. In this study the increased copy number of 8q was found in 8/9 (89%) of recurrent prostate cancers (FIG. 3E, FIG. 3F, FIG. 3G). Seven of these cases demonstrated gain of the entire q arm. However, in one case, the gain was limited to 8q24-qter. Seven tumors also showed loss of 8p. Six tumors showed both 8p loss and 8q gain, with two demonstrating 8q gain and only one 8p loss.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention.

More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following literature citations as well as those cited above are incorporated in pertinent part by reference herein for the reasons cited in the above text.

Alcaraz et al., "Aneuploidy and aneusomy of chromosome 7 detected by fluorescence in situ hybridization arc markers of poor progress in prostate cancer," Cancer Research, 55:3998–4002, 1994.

Bookstein et al., "Suppression of tumorigenicity of human prostate carcinoma cells by replacing a mutabed Rb gene," Science, 247:712–715, 1990.

Bookstein et al., "Promoter deletion and loss of retinoblastoma gene expression in human prostate carcinoma," Proc. Natl. Acad. Sci. USA 87:7762–7767, 1990.

Borg, et al., "HER-2/neu amplification predicts poor survival in node-positive breast cancer," Cancer Res. 50:4332–4337, 1990.

Boring et al., "Cancer Statistics 1993," CA Cancer J. Clin., 43:7–29, 1993.

Boring, C. C., "Cancer Statistics," CA Cancer J. Clin., 44:7–26, 1994.

Bova et al., "Homozygous deletion and frequent allelic loss of chromosome 8q22 loci in human prostate cancer," Cancer Research, 53:3869–3873, 1993.

Brodeur et al., "Amplification of N-myc in untreated human neuroblastomas correlates with advanced disease stage," Science, 224:1121–1124, 1984.

Brothman, et al., "Frequence and pattern of karyotypic abnormalities in human prostate cancer," Cancer Res., 50:3795–3803, 1990.

Carter and Coffey, "The prostate: An increasing medical problem," The Prostate, 16:39–48, 1990.

Carter and Coffey, "Prediction of tumor behavior in prostate cancer," In: J. P. Karr and M. Yamanak (eds.), Prostate Cancer: The Second Tokyo Symposium, pp. 19–27, New York: Elsevier, 1989.

Carter et al., "Allelic loss of chromosomes 16q and 10q in human prostate cancer," Proc. Natl. Acad. Sci. USA, 87:8751–8755, 1990.

Coffey, D. S., "Prostate cancer—an overview of an increasing dilemma," Cancer, (Phila.) 71 (Suppl.): 880–886, 1993.

Diamond et al., "A new method to assess metastatic potential of human prostate cancer: relative nuclear roundness," The Journal of Urology, 128:729–734, 1982.

Fleming et al., "Expression of the c-myc protooncogene in human prostatic carcinoma and genign prostatic hyperplasia," Cancer Research, 46:1535–1537, 1986.

Fukumoto et al., "Analysis of gene amplification in human tumor cell lines," Genetics, 85:6846–6850, 1988.

Futreal et al., "BRCA 1 mutations in primary breast and ovarian carcinomas," *Science*, 266:120, 1994.

Guan et al., "Identification of cryptic sites of DNA sequence amplification in human breast cancer by chromosome microdissection," *Nature Genetics*, 8:155–161, 1994.

Guan et al., "Generation of band-specific patining probes from a single microdissected chromosome." *Human Molecular Genetics*, 2:1117–1121, 1993.

Isaacs et al., "Wild-type p53 suppresses growth of human prostate cancer cells containing mutant p53 alleles," *Cancer Research*, 51:4716–4720, 1991.

Isaacs et al., "Molecular Biology of Prostate Cancer," *Seminars in Oncology*, 21:1–18, 1994.

Kallioniemi et al., "Comparative genomic hybridization for molecular cytogenetic analysis of solid tumors," *Science*, 258:818–821, 1992.

Kallioniemi et al., "Optimizing comparative genomic hybridization for analysis of DNA sequence copy number changes in solid tumors," *Genes Chrom. Cancer*, 10:231–243, 1994.

Kinzler et al., "Amplification units containing human N-myc and c-myc genes," *Proceedings of the National Academy of Sciences*, 83:1031–1035, 1986.

Lee, E. Y., "Tumor suppressor genes: a new era for molecular genetic studies of cancer," *Breast Cancer Res. Treat.*, 19:3–13, 1991.

Ludecke et al., "Cloning defined regions of the human genome by microdissection of banded chromosomes and enzymatic amplification," *Nature*, 338:348–350, 1989.

Lundgren et al., "Cytogenics of primary prostatic adenocarcinoma. Clonality and chromosome instability," *Cancer Genet. Cytogenet*, 61:165–173, 1992.

Macoska et al., "Fluorescence in situ hybridization analysis of 8p allelic loss and chromosome 8 instability in human prostate cancer," *Cancer Research*, 54:3824–3830, 1994.

McGill et al., "Double minute chromosomes are frequently found in tumors taken directly from patients," *Proc. Am. Assoc. Cancer Res.*, 33:40, 1992.

Meltzer et al., "Micro-FISH: A novel strategy to identify cytptic chromosomal rearrangements," *Nature Genetics*, 1:24–28, 1992.

Meltzer et al., "Rapid generation of region specific probes by chromosome microdissection and their application," *Nature Genetics*, 1:24–28, 1992.

Miki et al., "A strong candidate for the breast and ovarian cancer susceptibility gene BRCA1," *Science*, 266:66, 1994.

Milasin and Micic, "Double minute chromosomes in an invasive adenocarcinoma of the prostate," *Cancer Genet. Cytogenet.*, 72:157–159, 1994.

Morton et al., "Reduction of E-cadherin levels and deletion of the alpha-catenin gene in human prostate cancer cells," *Cancer Research*, 53:3585–3590, 1993.

Pearsons et al., "Use of fluorescent in situ hybridization for deoxyribonucleic acid ploidy analysis of prostatic adenocarcinoma," *J. Urol.*, 150:120–125, 1993.

Pinkel et al., "Cytogenetic analysis using quantitative, high sensitivity, fluorescence hybridization," *Proc. Natl. Acad. Sci. USA*, 83:2934–2938, 1986.

Ruckle et al., "Prostate-specific antigen: Concepts for staging prostate cancer and monitoring response to therapy," *Mayo Clin. Proc.*, 69:69–79, 1994.

Takahashi et al., "Potential markers of prostate cancer aggressiveness detected by fluorescence in situ hybridization in needle biopsies," *Cancer Research*, 54:3574–3579, 1994.

Trent and Thompson, "Methods for chromosome banding of human and experimental tumors in vitro," In: Methods in Enzymology, Academic Press, New York, (Molecular Genetics of Mammalian Cells, 151:267–279, 1987.

Umbas et al., "Expression of the cellular adhesion molecule E-cadherin is reduced or absent in high-grade prostate cancer," *Cancer Research*, 52:5104–5109, 1992.

Visakorpi et al., "Sensitive detection of chromosome copy number aberrations in prostate cancer by fluorescence in situ hybridization," *American Journal of Pathology*, 145:1–7, 1994.

Ware et al., "Production of monoclonal antibody alpha Pro3 recognizing a human prostatic carcinoma antigen," *Cancer Res.*, 42:1215–1222, 1982.

Whittemore, A. S., "Prostate cancer in Cancer Survey, Trends in Cancer Incidence and Mortality vol.19/20 p.309–322, ed E. Sidebottom, Cold Spring Harbor Laboratory Press, 1994.

Zhang et al., "Rapid isolation and characterization of amplified DNA by chromosome microdissection: Identification of IGFIR amplification in malignant melanoma," *Oncogene*, 8:2827–2831, 1993.

Zhang et al., "Whole genome amplification from a single cell: Implication for genetic analysis," *Proc. Natl. Acad. Sci. USA*, 89:5847–5851, 1992.

---

What is claimed is:

1. A method of diagnosing prostate cancer progression, comprising:
   determining the presence of an amplified 8q24.1–24.2 chromosome band segment from a human prostate tumor sample wherein said amplified 8q24.1–24.2 chromosome band segment is indicative of prostate cancer progression.

2. The method of claim 1, wherein the determining comprises hybridization of the 8q24.1–24.2 segment with a probe.

3. The method of claim 2, wherein said probe is an oligonucleotide mixture of DNA segments that is complementary to gene segment 8q24.1–24.2.

4. The method of claim 2, wherein said probe is a labeled probe.

5. A method of detecting recurrent prostate cancer comprising obtaining a prostate tumor DNA sample from a patient suspected of having recurrent prostate cancer and determining DNA sequence copy number changes in chromosome segment 8q wherein a gain in copy number relative to copy number of normal 8q DNA is indicative of prostate cancer recurrence.

6. The method of claim 5, wherein the prostate tumor sample DNA sample is obtained by chromosome microdissection.

7. The method of claim 5, wherein chromosome segment 8q is further defined as 8q24.

8. The method of claim 5, wherein chromosome segment 8q is further defined as 8q24.1–24.2.

9. The method of claim 6, wherein determining DNA sequence copy number changes is accomplished using a probe.

10. The method of claim 9, wherein said probe is a labeled probe hybridized to chromosome 8 DNA.

11. The method of claim 10, wherein said probe is fluorescently-labeled.

12. The method of claim 11, wherein the intensity of said labeled probe is determined using a digital image analysis system.

13. The method of claim 1, wherein said chromosome band segment is obtained by chromosome microdissection.

14. The method of claim 2, wherein said probe is identified as a DNA segment complementary to gene segment 8q24.1–24.2.

15. The method of claim 2, wherein said probe is a degenerate probe.

16. The method of claim 4, wherein said labeled probe is a fluorescently-labeled probe.

17. The method of claim 4, wherein said labeled probe is a radioactively-labeled probe.

18. The method of claim 9, wherein said probe is a degenerate probe.

19. The method of claim 9, wherein said probe is an oligonucleotide mixture of DNA segments that is complementary to gene segment 8q24.1–24.2.

20. The method of claim 10, wherein said labeled probe is a radioactively-labeled probe.

21. The method of claim 10, wherein chromosome 8 DNA is further identified as chromosome 8q DNA.

22. The method of claim 16, wherein said probe is detected using a digital image analysis system.

23. The method of claim 21, wherein chromosome 8q DNA is further identified as chromosome 8q24 DNA.

24. The method of claim 22, wherein chromosome 8q24 DNA is further identified as chromosome 8q24.1–24.2 DNA.

* * * * *

UNITED STATES PATENT AND TRADEMARK OFFICE
CERTIFICATE OF CORRECTION

PATENT NO.    :    5,658,730

DATED         :    August 19, 1997

INVENTOR(S)   :    John McGill, Carla Van Den Berg, Jeffrey Trent, Daniel Von Hoff and Paul Meltzer It is certified that error appears in the above-identified patent and that said Letters Patent is hereby corrected as shown below:

On the title page, item:

[73] Assignee:     CTRC Research Foundation, San Antonio, Tex.
Regents of The University of Michigan, Ann Arbor, Mich.

Signed and Sealed this

Thirtieth Day of December, 1997

*Attest:*

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,658,730
DATED : August 19, 1997
INVENTOR(S) : McGill et al.

It is certified that error appears in the above-identified patent and that said Letters Patent is hereby corrected as shown below:

<u>Title page,</u>
Item [73], Assignee, add the following -- Michigan, University of, Regents, The --.

Signed and Sealed this

Twenty-ninth Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 5,658,730
APPLICATION NO. : 08/376364
DATED : August 19, 1997
INVENTOR(S) : McGill et al.

It is certified that error appears in the above-identified patent and that said Letters Patent is hereby corrected as shown below:

Title page,
Item [75], Inventors, add the following -- Robert Jenkins --.

Signed and Sealed this

Fifteenth Day of September, 2009

David J. Kappos
*Director of the United States Patent and Trademark Office*